United States Patent

Yamaura

(10) Patent No.: US 8,691,984 B2
(45) Date of Patent: Apr. 8, 2014

(54) METHOD OF STORING TRIALLYL ISOCYANURATE

(75) Inventor: Mabuko Yamaura, Fukushima-ken (JP)

(73) Assignee: Nippon Kasei Chemical Company Limited, Iwaki-shi, Fukushima-ken (JP)

( * ) Notice: Subject to any disclaimer, the term of this patent is extended or adjusted under 35 U.S.C. 154(b) by 240 days.

(21) Appl. No.: 13/287,283

(22) Filed: Nov. 2, 2011

(65) Prior Publication Data

US 2012/0095225 A1   Apr. 19, 2012

Related U.S. Application Data

(63) Continuation-in-part of application No. PCT/JP2010/058567, filed on May 20, 2010.

(30) Foreign Application Priority Data

May 25, 2009   (JP) ................................. 2009-125335

(51) Int. Cl.
| | | |
|---|---|---|
| C07D 251/34 | (2006.01) | |
| C07D 251/26 | (2006.01) | |
| C07D 239/30 | (2006.01) | |
| C07D 239/34 | (2006.01) | |
| C08F 26/06 | (2006.01) | |
| C08K 5/3492 | (2006.01) | |

(52) U.S. Cl.
USPC ......................................... 544/221; 544/313

(58) Field of Classification Search
USPC ....................................................... 544/221
See application file for complete search history.

(56) References Cited

U.S. PATENT DOCUMENTS

2009/0312545 A1   12/2009   Werle et al.

FOREIGN PATENT DOCUMENTS

| JP | 47-22588 | 6/1972 |
| JP | 48-26022 | 8/1973 |
| JP | 11-255753 | 9/1999 |
| JP | 2000-234037 | 8/2000 |
| JP | 2004-168884 | 6/2004 |
| WO | WO 2008/006661 | 1/2008 |

OTHER PUBLICATIONS

International Search Report for PCT/JP2010/058567, mailed Aug. 17, 2010.
English language translation of the International Preliminary Report on Patentability and Written Opinion in PCT/JP2010/058567 dated Dec. 22, 2011.

*Primary Examiner* — Venkataraman Balasubramanian
(74) *Attorney, Agent, or Firm* — Nixon & Vanderhye P.C.

(57) ABSTRACT

The present invention provides a method of storing TAIC in which TAIC is prevented from suffering from freezing and solidification during storage thereof in the winter season. In the method of the present invention, the triallyl isocyanurate is mixed with a silane coupling agent to prepare a composition comprising both thereof, and the resulting composition is stored. In the preferred embodiment of the present invention, the silane coupling agent is used in an amount of 5 to 30% by weight based on the weight of the triallyl isocyanurate, and γ-methacryloxypropyl trimethoxysilane is used as the silane coupling agent.

5 Claims, No Drawings

METHOD OF STORING TRIALLYL ISOCYANURATE

This application is a Continuation-In-Part of International Application No. PCT/JP2010/058567 filed May 20, 2010 which designated the U.S. and claims priority to JP Patent Application No. 2009-125335 filed May 25, 2009, the entire contents of each of which are hereby incorporated by reference.

TECHNICAL FIELD

The present invention relates to a method of storing triallyl isocyanurate. The triallyl isocyanurate is hereinafter referred to merely as "TAIC".

BACKGROUND ART

TAIC is useful as a crosslinking agent having excellent heat resistance and chemical resistance, and it is expected to use TAIC in extensive applications such as electronic materials, liquid crystals, semiconductors and solar cells. For example, in printed circuit boards, i.e., plate- or film-shaped members constituting electronic circuits in which a number of electronic parts such as integrated circuits, resistors and capacitors are fixed on a surface thereof and connected to each other through wirings, there is proposed the method in which TAIC is used as a sealing material for preventing penetration of substances such as liquids and gases into the respective electronic parts (Patent Document 1). In such a proposed method, TAIC is used as a liquid sealing material because the TAIC is present in the form of a viscous liquid (melting point: 26° C.) at an ordinary temperature. In addition, in order to enhance a wettability of TAIC, a silane coupling agent is added thereto. Also, TAIC is used as a crosslinking agent for crosslinkable polymers (Patent Document 2).

Meanwhile, TAIC having a melting point of 26° C. tends to be frozen and solidified during storage thereof in the winter season. In particular, when TAIC is stored in a relatively large container (drum), there tends to arise such a problem that it takes a considerably long time until the frozen TAIC is melted by heating. Further, when the treating temperature of TAIC is lowered, the viscosity of TAIC is rapidly increased, resulting in deteriorated handling property thereof.

PRIOR DOCUMENTS

Patent Documents

Patent Document 1: Japanese Patent Application Laid-Open (KOKAI) No. 2007-115840
Patent Document 2: Japanese Patent Application Laid-Open (KOKAI) No. 2006-036876

SUMMARY OF THE INVENTION

Problems To Be Solved By the Invention

The present invention has been accomplished in view of the above conventional problems. An object of the present invention is to provide a method of storing TAIC in which TAIC is free from freezing and solidification during storage thereof in the winter season.

Means For Solving Problems

As a result of the present inventors' earnest study for achieving the above object, it has been found that when a silane coupling agent to be added as a wettability improver upon use is previously added to TAIC when stored prior to the use, the melting point of TAIC is lowered so that TAIC is prevented from suffering from freezing and solidification during the storage in the winter season. Thus, the present invention has been attained.

The present invention has been completed on the basis of the above finding. In an aspect of the present invention, there is provided a method of storing triallyl isocyanurate, comprising the steps of mixing the triallyl isocyanurate with a silane coupling agent to prepare a composition comprising both thereof, and storing the resulting composition.

Effect of the Invention

According to the present invention, TAIC can be prevented from suffering from freezing and solidification during storage thereof in the winter season. As a result, it is possible to treat TAIC without conducting heating and melting procedures even in the winter season, and further the stored TAIC exhibits a good handling property upon use because the viscosity thereof is not increased even after stored.

PREFERRED EMBODIMENTS FOR CARRYING OUT THE INVENTION

The present invention is described in detail below.

First, TAIC to be treated according to the present invention is described. As the industrial process for production of TAIC, there are known the following three production processes.

(1) The production process in which 2,4,6-trichloro-1,3,5-triazine (cyanuric chloride) and allyl alcohol are reacted with each other to obtain triallyl cyanurate (hereinafter referred to merely as "TAC"), and then the thus obtained TAC is subjected to rearrangement reaction (TAC rearrangement method).

(2) The production process in which allyl chloride and sodium cyanate are reacted to obtain allyl isocyanate, and then the thus obtained allyl isocyanate is subjected to trimerization (sodium cyanate method).

(3) The production process in which allyl chloride and isocyanuric acid (a tautomer of cyanuric acid) are reacted in the presence of a base catalyst (isocyanuric acid method).

The TAIC to be treated according to the present invention may be produced by any of the above methods. Meanwhile, although no impurities included in TAIC obtained by the above respective production methods have conventionally been reported, it is required that the impurities which may cause metal corrosion are removed from TAIC to reduce their content to as small a level as possible. In the present invention, from the above viewpoints, the following TAIC products are recommended. Since the impurities included in TAIC vary depending upon the production process thereof, preferred TAIC to be treated according to the present invention is described with respect to the respective production processes.

[TAIC Produced By TAC Rearrangement Method]

In the rearrangement method, TAIC may be produced, for example, according to the following reaction route in which 2,4,6-trichloro-1,3,5-triazine (cyanuric chloride) is reacted with allyl alcohol to obtain triallyl cyanurate (TAC) ("JACS", Vol. 73, 2986-2990), and then the thus obtained TAC is subjected to rearrangement reaction (Japanese Patent Publication (KOKOKU) No. 4-6570 (1992)).

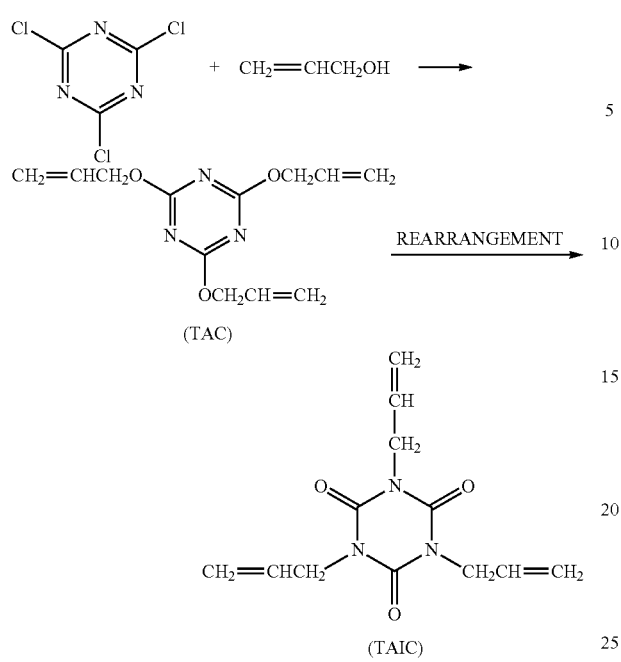

(TAC)

(TAIC)

As a result of the present inventors' earnest study on the impurities included in TAIC obtained by the rearrangement method, the following knowledges have been attained.

(1) Impurities included in TAIC produced from TAC as a raw material are also present in TAC. The impurities included in TAC are represented by the following chemical formulae (I), (II) and (III).

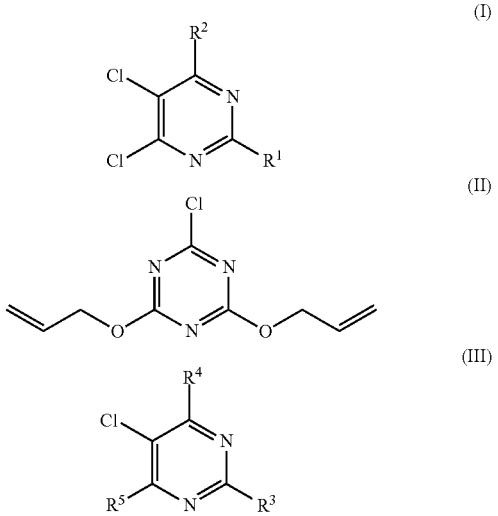

In the chemical formula (I), $R^1$ and $R^2$ are respectively a chlorine atom or an allyloxy group with the proviso that at least one of $R^1$ and $R^2$ is a chlorine atom. In the chemical formula (III), optional one of $R^3$, $R^4$ and $R^5$ is a chlorine atom, and optional two of $R^3$, $R^4$ and $R^5$ are allyloxy groups.

(2) The compounds represented by the chemical formulae (I) and (III) are respectively in the form of an allylated product of chlorinated barbituric acid (2,4,5,6-tetrachloropyrimidine). The reason for production of these compounds is considered as follows. That is, cyanuric chloride is usually produced by trimerization of chlorocyanogen obtained by chlorination of prussic acid. However, if impurities such as acetylene are present in prussic acid as the raw material, tetrachlorobarbituric acid represented by the following chemical formula (IV) is produced. By the reaction between the above 2,4,5,6-tetrachloropyrimidine and allyl alcohol, the organic chlorine compounds represented by the above chemical formulae (I) and (III) are produced as impurities.

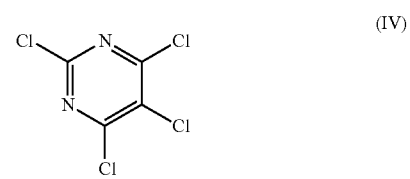

(3) It is suggested that the organic chlorine compound represented by the chemical formula (II) is a by-product obtained from the reaction between cyanuric chloride and allyl alcohol.

(4) The organic chlorine compounds represented by the chemical formulae (I) and (II) are gradually hydrolyzed in water to generate chlorine ions which may cause corrosion, whereas the organic chlorine compound represented by the chemical formula (III) is subjected to substantially no hydrolysis and therefore produces no substances causing corrosion. Accordingly, the organic chlorine compounds represented by the chemical formulae (I) and (II) are identified to be corrosive substances.

(5) When TAIC is produced from TAC comprising the organic chlorine compounds represented by the chemical formulae (I) and (II) as the raw material, the organic chlorine compound represented by the chemical formula (I) remains in TAIC as produced and may cause corrosion. That is, the organic chlorine compound represented by the chemical formula (II) is decomposed and removed during the production and purification steps of TAIC, so that the organic chlorine compound represented by the chemical formula (I) becomes substantially only one corrosive substance in TAIC. It is impossible to remove the corrosive substance by water-washing or distillation. However, the corrosive substance can be removed by subjecting it to hydrolysis under specific conditions. After removing the corrosive substance by the hydrolysis, TAC is subjected to rearrangement reaction, thereby enabling production of TAIC comprising a less amount of corrosive substances.

Accordingly, in the present invention, it is recommended that TAIC comprises the organic chlorine compound represented by the above chemical formula (I) in an amount of not more than 100 ppm. The content of the organic chlorine compound represented by the above chemical formula (I) in the TAIL is preferably not more than 50 ppm and more preferably not more than 30 ppm.

The production of the above TAC, i.e., the reaction between cyanuric chloride and allyl alcohol, is carried out under heating in the presence of a basic catalyst (for example, sodium hydroxide). In general, TAC is produced by adding cyanuric chloride to a solution comprising allyl alcohol in an effective amount as a reaction solvent, and given amounts of the basic catalyst and water at room temperature and then stirring the obtained mixture for a predetermined time. The details of the reaction conditions can be recognized by referring to the above "JACS", Vol. 73, 2986-2990 (1951). The thus obtained crude TAC comprises the organic chlorine compounds represented by the above chemical formulae (I) and (II). The content of the organic chlorine compound represented by the chemical formula (I) in the crude TAC is usually 100 to 250 ppm, whereas the content of the organic chlorine compound represented by the chemical formula (II) in the crude TAC is usually 500 to 1,000 ppm.

In order to selectively hydrolyze only the organic chlorine compounds represented by the chemical formulae (I) and (II) without decomposing TAC, the crude TAC is treated in a strong base aqueous solution having a low concentration at a relatively low temperature. More specifically, the treatment of the crude TAC is carried out as follows.

That is, a salt precipitated from a TAC production reaction solution (for example, sodium chloride) is first removed by filtration to recover a filtrate therefrom. The thus recovered filtrate is concentrated to recover a crude TAC as an oily material. Next, the crude TAC (the above oily material) is subjected to stirring treatment in the strong base aqueous solution having a concentration of usually 0.5 to 10% by weight and preferably 1 to 5% by weight at a temperature of usually 30 to 80° C. and preferably 30 to 60° C. The treating time is usually 0.5 to 10 hr and preferably 1 to 6 hr. When the respective treating conditions are less than the above-specified ranges, it may be difficult to hydrolyze the organic chlorine compounds represented by the above chemical formulae (I) and (II). When the respective treating conditions are more than the above-specified ranges, TAC tends to be hydrolyzed.

The production of the above TAIC, i.e., the rearrangement reaction of TAC, is carried out by heat-treating TAC in the presence of a catalyst. The details of the reaction conditions can be recognized by referring to the above Japanese Patent Publication (KOKOKU) No. 4-6570 (1992). In the preferred embodiment of the present invention, the rearrangement reaction is carried out in a reaction solvent (for example, xylene) in the presence of a copper catalyst. The reaction temperature is usually 100 to 150° C. and preferably 120 to 140° C. After completion of the reaction, the reaction solvent is distilled off under reduced pressure to recover an oily material. The thus recovered oily material is subjected to distillation under reduced pressure to obtain crystals of TAIC.

[TAIC Produced By Sodium Cyanate Method Or Isocyanuric Acid Method]

As a result of the present inventors' earnest study on the impurities included in TAIC obtained by the rearrangement method, the following knowledges have been attained.

(1) The TAIC obtained by the sodium cyanate method or the isocynauric acid method comprises, as one of impurities, an organic chlorine compound represented by the following chemical formula (V). The organic chlorine compound is gradually hydrolyzed in water to generate chlorine ions which may cause corrosion.

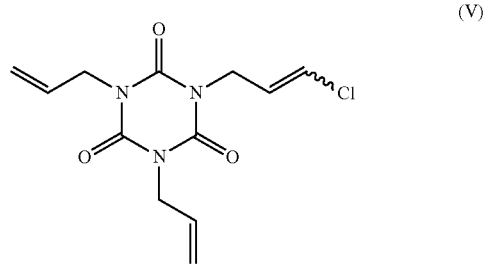 [SMILES: C=CCn1c(=O)n(CC=C)c(=O)n(CC=CCl)c1=O]

(V)

wherein a bond expressed by a wavy line indicates that the organic chlorine compound is a cis-type compound, a trans-type compound or a mixed bond comprising the cis-type and trans-type compounds at an optional ratio, and this is hereinafter defined in the same way.

(2) The organic chlorine compound represented by the chemical formula (V) is produced by the reaction between sodium cyanate and 1,3-dichloropropene represented by the following chemical formula (VI) which is included as impurity in allyl chloride. The organic chlorine compound represented by the chemical formula (V) is also produced by the reaction between cyanuric acid and 1,3-dichloropropene.

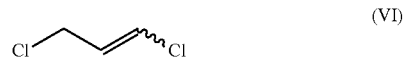

(VI)

(3) The organic chlorine compound represented by the chemical formula (V) is hardly removed by separation methods such as distillation, whereas the 1,3-dichloropropene represented by the chemical formula (VI) can be readily separated from allyl chloride by subjecting the allyl chloride to distillative purification.

Accordingly, in the present invention, it is recommended that TAIC comprises the organic chlorine compound represented by the above chemical formula (V) in an amount of not more than 500 ppm.

The above TAIC may be basically produced by the known sodium cyanate method or by the known isocyanuric acid method.

In the sodium cyanate method, allyl chloride and sodium cyanate are reacted with each other to obtain allyl isocyanate, and then the thus obtained allyl isocyanate is subjected to trimerization. The details of the reaction conditions can be recognized, for example, by referring to Japanese Patent Publication (KOKOKU) No. 58-35515 (1983). In the preferred embodiment of the present invention, allyl chloride is added dropwise into a solution comprising sodium cyanate, calcium chloride, potassium bromide and DMF, and then the resulting reaction mixture is reacted and aged at a temperature of 100 to 150° C. for 0.5 to 5 hr.

In the isocyanuric acid method, allyl chloride and isocyanuric acid are reacted in the presence of a base catalyst. The details of the reaction conditions can be recognized, for example, by referring to U.S. Pat. No. 3,065,231. In the preferred embodiment of the present invention, allyl chloride is added dropwise into a solution comprising isocyanuric acid, DMF and triethylamine, and then the resulting reaction mixture is reacted and aged at a temperature of 100 to 150° C. for 0.5 to 5 hr.

In any of the above methods, it is important that the allyl chloride used as the raw material has a content of 1,3-dichloropropene (content of a cis-type compound, a trans-type compound or a mixture comprising the cis-type and trans-type compounds at an optional ratio) of not more than 200 ppm. The industrially used allyl chloride usually comprises impurities such as propyl chloride, 1,2-dichloropropene, 1,3-dichloropropane and 1,3-dichloropropene. Allyl chloride comprising 1,3-dichloropropene in an amount of not more than 200 ppm may be produced by subjecting the industrially used allyl chloride to rectification. The number of theoretical plates in a distillation column used for the rectification is usually not less than 50 plates and preferably 60 to 90 plates. The reflux ratio is usually not less than 5 and preferably 7 to 10. The content of 1,3-dichloropropene (content of a cis-type compound, a trans-type compound or a mixture comprising the cis-type and trans-type compounds at an optional ratio) in the allyl chloride is preferably not more than 100 ppm.

Next, the silane coupling agent used in the present invention is explained. As the silane coupling agent, there may be mentioned those silane coupling agents comprising a group selected from the group consisting of an unsaturated group such as a vinyl group and a methacryloxy group, a haloalkyl group, an amino group, a mercapto group and an epoxy group, as well as a hydrolyzable group such as an alkoxy group and an acyl group. Specific examples of the silane coupling agent include vinyl triethoxysilane, vinyl tris(β-methoxyethoxy)silane, vinyl triacetoxysilane, γ-methacryloxypropyl trimethoxysilane, N-(β-aminoethyl)-γ-aminopropyl trimethoxysilane, N-(β-aminoethyl)-γ-aminopropylmethyl dimethoxysilane, γ-aminopropyl triethoxysilane, γ-glycidoxypropyl trimethoxysilane and γ-mercaptopropyl triethoxysilane. Among these silane coupling agents, γ-methacryloxypropyl trimethoxysilane is especially suitably used.

The method of mixing TAIC and the silane coupling agent to prepare a composition comprising both TAIC and the silane coupling agent is not particularly limited. However, the method of mixing both the components at a temperature of 20 to 50° C. is preferred. TAIC products obtained by removing the above impurities which may cause metal corrosion are finally produced through a distillation step even when they are produced by any of the above methods. Therefore, it is convenient that TAIC which is recovered from the distillation step and has a relatively high temperature is mixed with the silane coupling agent. The silane coupling agent may be usually added to TAIC, but TAIC may be added to the silane coupling agent. The atmosphere used upon the mixing may be usually atmospheric air, or may be a nitrogen atmosphere, if required. The mixing may be carried out using an ordinary stirrer.

The silane coupling agent may be used based on TAIC in such an amount as required for reducing a melting point of TAIC to a temperature of not higher than 20° C. When the amount of the silane coupling agent used is too large, the concentration of TAIC in the composition tends to be lowered, so that when using the composition as such, TAIC may fail to exhibit a sufficient effect as a sealing material or a crosslinking agent. Therefore, the amount of the silane coupling agent used based on TAIC is usually 5 to 30% by weight and preferably 10 to 20% by weight. From the viewpoint of using the TAIC composition as a sealing material or a crosslinking agent, in the case where the amount of the silane coupling agent used is too large, the resulting silane-coupling agent-containing TAIC which is stored according to the present invention may also be used as a master batch. That is, the master batch may be diluted with TAIC containing no silane coupling agent upon use.

As facilities for storing the TAIC composition, there may be used special facilities such as a storage tank. Alternatively, in view of transportation or handling property, there may also be used, for example, 18 L rectangular metallic cans (itto cans) and large metallic cans (drums) having a capacity of 200 L or more.

According to the present invention, since TAIC is prevented from suffering from freezing and solidification during storage thereof in the winter season, it is possible to treat the TAIC without conducting any heating and melting procedures even in the winter season. In addition, since the TAIC stored does not exhibit a high viscosity, there can be obtained the above effect of allowing the TAIC to exhibit a good handling property when treated. The above TAIC as recommended according to the present invention which has a less content of the impurities which may cause metal corrosion can be suitably used as a sealing material for printed circuit boards. Further, the TAIC according to the present invention may be mixed with a crosslinkable elastomer and then cured by heating or radiation, and the resulting cured product can be used as a sealing material for electronic materials, semiconductors, solar cell materials, etc. Furthermore, the TAIC according to the present invention may be mixed with a crosslinkable thermoplastic resin and then cured by irradiation with electron beams, etc., and the resulting cured product can be suitably used for coating electric wires, etc.

EXAMPLES

The present invention is described in more detail below by Examples. However, these Examples are only illustrative and not intended to limit the present invention thereto, and various changes or modifications are possible unless they depart from the scope of the present invention. Meanwhile, the analyzing methods used in the following Examples and Comparative Examples are as follows.

(1) Analysis of Organic Chlorine Compounds Represented By the Chemical Formulae (I) And (II)

The analysis of the organic chlorine compounds were carried out using a gas chromatograph (by an area percentage method). The conditions for the analysis are shown in Table 1. Meanwhile, a detection limit of the measuring device used was 10 ppm.

TABLE 1

| | |
|---|---|
| Device name | "HP6850" manufactured by Agilent Inc. |
| Column name | Capillary column "BPX-5" (60 m × 0.32 mm; film thickness: 0.25 μm) manufactured by SGE Inc. |
| Column temperature | 50° C. (held for 5 min) to 350° C. (at a temperature rise rate of 10° C./min) |
| Injection port temperature | 250° C. |
| Detector temperature | 300° C. |
| Pressure | 150 kPa |
| Split ratio | 20 |
| Solvent | Acetone |
| Concentration of sample | 20% by weight |

(2) Analysis of 1,3-dichloropropene

The analysis of the 1,3-dichloropropene was carried out by single ion monitoring method (SIM method) using GC-MS (Gas Chromatograph-Mass Spectrometry). The analyzing conditions are shown in Table 2 below. Meanwhile, the detection limit of the measuring device used was 0.5 ppm. In Comparative Example 1, a sample of 1,3-dichloropropene to be analyzed was used in the form of a dilute solution prepared by diluting the 1,3-dichloropropene by 20 times.

TABLE 2

| | |
|---|---|
| Device name | "QP-2010" manufactured by Shimadzu Seisakusho Corp. |
| Column name | Capillary column "HP-5" (30 m × 0.32 mm; film thickness: 0.25 μm) manufactured by Agilent Inc. |
| Column temperature | 50° C. |
| Injection port temperature | 250° C. |
| Ion source temperature | 230° C. |
| Ion source | EI |
| Pressure | 130 kPa |
| SIM method | m/z 75, 110 |

(3) Analysis of Organic Chlorine Compound of Chemical Formula (V)

The analysis of the organic chlorine compound of the chemical formula (V) was carried out using a gas chromatograph (by an area percentage method). The analyzing conditions are shown in Table 3 below. Meanwhile, a detection limit of the measuring device used was 10 ppm.

TABLE 3

| Device name | "GC-17A" manufactured by Shimadzu Seisakusho Corp. |
|---|---|
| Column name | Capillary column "DB-225" (30 m × 0.25 mm; film thickness: 0.25 μm) manufactured by J&W Inc. |
| Column temperature | 150° C. to 220° C. (at a temperature rise rate of 2° C./min) |
| Injection port temperature | 250° C. |
| Detector temperature | 300° C. |
| Pressure | 150 kPa |
| Split ratio | 20 |
| Solvent | Acetone |
| Concentration of sample | 5% by weight |

Comparative Production Example 1

A solution comprising 100 g of allyl alcohol, 12 g of NaOH and 10 g of water was mixed with 18.4 g of cyanuric chloride at room temperature. The resulting mixture was stirred at room temperature for 2 hr, and sodium chloride precipitated was removed by filtration to recover a filtrate. The thus recovered filtrate was concentrated to obtain an oily material. Next, the thus obtained oily material was washed with water and then subjected to distillative purification to obtain crystals of TAC (yield: 85%). The thus obtained TAC comprised 170 ppm of a mixture (A) comprising an organic chlorine compound of the chemical formula (I) in which $R^1$ is an allyoxy group and $R^2$ is a chlorine atom (2-allyoxy-4,5,6-trichloropyrimidine) and an organic chlorine compound of the chemical formula (I) in which $R^1$ is a chlorine atom and $R^2$ is an allyoxy group (4-allyoxy-2,5,6-trichloropyrimidine), and 740 ppm of an organic chlorine compound of the chemical formula (II) (2,6-diallyloxy-4-chlorotriazine).

Next, 24.9 g of the above TAC and 3.4 g of cupric chloride hydrate were added to 120 g of xylene, and the resulting mixture was stirred at 120° C. for 2 hr to subject the TAC to rearrangement reaction. Thereafter, the obtained reaction solution was cooled and placed under reduced pressure to distil off xylene therefrom, thereby obtaining an oily material. Next, the thus obtained oily material was subjected to distillation under a reduced pressure of 0.1 Torr at 115° C. to obtain crystals of TAIC (yield: 90%). The thus obtained TAIC comprised 120 ppm of the mixture (A) of the organic chlorine compounds and 10 ppm of the organic compound of the chemical formula (II).

Production Example 1

The oily material produced in the same manner as defined in Comparative Production Example 1 was subjected to heating and stirring treatment in a 5% by weight NaOH aqueous solution at 50° C. for 2 hr. Next, the obtained reaction solution was neutralized with hydrochloric acid, and an organic layer was separated therefrom and then subjected to distillative purification to obtain crystals of TAC (yield: 84%). It was confirmed that neither the mixture (A) of the organic chloride compounds nor the organic chloride compound of the chemical formula (II) were detected in the thus obtained TAC (less than 10 ppm).

Next, the above TAC was subjected to the same procedure subsequent to the rearrangement reaction as defined in Comparative Production Example 1, thereby obtaining TAIC (yield: 90%). It was also confirmed that neither the mixture (A) of the organic chloride compounds nor the organic chloride compound of the chemical formula (II) were detected in the thus obtained TAIC (less than 10 ppm).

Production Example 2

The oily material produced in the same manner as defined in Comparative Production Example 1 was subjected to heating and stirring treatment in a 1% by weight NaOH aqueous solution at 50° C. for 6 hr. Next, the obtained reaction solution was neutralized with hydrochloric acid, and an organic layer was separated therefrom and then subjected to distillative purification to obtain crystals of TAC (yield: 84%). It was confirmed that the thus obtained TAC comprised 40 ppm of the mixture (A) of the organic chloride compounds and 10 ppm of the organic chloride compound of the chemical formula (II).

Next, the above TAC was subjected to the same procedure subsequent to the rearrangement reaction as defined in Comparative Production Example 1, thereby obtaining TAIC (yield: 90%). It was confirmed that the thus obtained TAIC comprised 10 ppm of the mixture (A) of the organic chloride compounds, but no organic chloride compound of the chemical formula (II) was detected therein (less than 10 ppm).

Comparative Production Example 2

A solution comprising 100 g of sodium cyanate, 14 g of calcium chloride, 13 g of potassium bromide and 500 g of DMF was maintained at 120° C., and 98 g of allyl chloride (1,3-dichloropropene comprising 140 ppm of a cis isomer and 140 ppm of a trans isomer) were added dropwise to the solution over 1 hr. The resulting reaction solution was further reacted and aged at 130° C. for 3 hr, and then subjected to distillation under reduced pressure at 100° C. to remove the solvent therefrom, thereby obtaining an oily material. Next, the thus obtained oily material was washed with a concentrated hydrochloric acid and then with water, and the washing treatments with the concentrated hydrochloric acid and water was respectively repeated two times (at a temperature of 60° C. for each treatment). Then, the obtained organic layer was subjected to distillation under reduced pressure (under 0.1 Torr at 115° C.) to obtain TAIC in the form of a viscous liquid (yield: 90%). It was confirmed that the thus obtained TAIC comprised the organic chlorine compound represented by the chemical formula (V) in an amount of 590 ppm.

Production Example 3

The same procedure as defined in Comparative Production Example 2 was conducted except that in Comparative Production Example 2, allyl chloride comprising 1,3-dichloropropene (comprising 0.1 ppm of a cis isomer and 0.1 ppm of a trans isomer) was used as the raw material, thereby producing TAIC (yield: 91%). As a result, it was confirmed that no organic chloride compound represented by the general formula (V) was detected in the thus obtained TAIC (less than 10 ppm).

Experimental Example 1 (Hydrolysis Test of TAIC)

A Teflon (registered trademark) pressure container was charged with 1 g of each of the TAICs obtained in the above Examples, etc., and 20 g of water, and the contents of the container were heated at 120° C. for 200 hr to measure a chlorine ion concentration in water. The measurement of the chlorine ion concentration in water was carried out using an ion chromatograph (column used: "DIONEX Ion Pack AS12A"; eluent used: 2.7 mM-$Na_2CO_3$/0.3 mM-$NaHCO_3$). The detection limit of the measuring device used was 1 ppm. The results are shown in Table 4.

TABLE 4

| Kind of TAIC | Chlorine ion concentration (ppm) |
|---|---|
| Comparative Production Example 1 | 237 |
| Production Example 1 | ND (less than 1 ppm) |
| Production Example 2 | 21 |
| Comparative Production Example 2 | 150 |
| Production Example 3 | ND (less than 1 ppm) |

Experimental Example 2 (Hydrolysis of Corrosive Substance)

According to the following procedure, the corrosive substance was synthesized, and subjected to hydrolysis under accelerated conditions.
<Corrosive Substance: Synthesis of 2-allyoxy-4,5,6-trichloropyrimidine>

Into a solution comprising 54.04 g (0.2361 mol) of 2,4,5,6-tetrachloropyrimidine produced by Tokyo Chemical Industry Co., Ltd., 12.93 g (0.3070 mol) of NaOH and 280 g of 1,4-dioxane, were added dropwise 18.01 g (0.3070 mol) of allyl alcohol at 40° C. over 2 hr. Further, the reaction mixture was reacted at 40° C. for 2.5 hr, cooled and then subjected to filtration to distil off dioxane in vacuo. The resulting reaction product was purified by silica gel chromatography (ethyl acetate/n-hexane=1/1), thereby obtaining 53.34 g of 2-allyloxy-4,5,6-trichloropyrimidine (yield: 93.5% by weight). The identification of the reaction product was carried out by GC-MS analysis. For reference, the measurement results of the GC-MS analysis are shown in Table 5 below.

TABLE 5

| GC-MS (EI mode) | m/e 41, 73, 85, 108, 120, 163, 182, 203, 223, 240 |
|---|---|
| GC-MS (CI mode) | (M + 1) 239 |

<Hydrolysis>
A pressure container was charged with 5 g of the above corrosive substance and 5 g of of water, and the contents of the container were heated at 140° C. for 6 days. As a result, it was confirmed that the resulting hydrolyzed product had a chlorine ion concentration of 15% by weight.

Examples 1 and 2

The following two kinds of commercially available TAICs, i.e., TAIC (1) and TAIC (2), were used as the TAIC.
<TAIC (1)>
TAIC comprising 120 ppm of the mixture (A) comprising the organic chlorine compound of the chemical formula (I) in which $R^1$ is an allyloxy group and $R^2$ is a chlorine atom (2-allyoxy-4,5,6-trichloropyrimidine), and the organic chlorine compound of the chemical formula (I) in which $R^1$ is a chlorine atom and $R^2$ is an allyloxy group (4-allyloxy-2,5,6-trichloropyrimidine), and 10 ppm of the organic chlorine compound of the chemical formula (II).
<TAIC (2)>
TAIC comprising less than 10 ppm of the organic chlorine compound of the chemical formula (V).

γ-Methacryloxypropyl trimethoxysilane (KBM) in an amount as shown in Table 7 was added to 100 parts by weight of the above respective TAICs, and the resulting mixture was stirred at 50° C. for 30 min to obtain a composition. The melting point of the thus obtained composition was measured. The results are shown in Table 7. The measurement of the melting point was conducted by solidifying the composition at −30° C. and subjecting the solidified composition to DSC to determine the melting point thereof. The measuring conditions are shown in Table 6.

TABLE 6

| (Measuring conditions of melting point) | |
|---|---|
| Device name | Differential scanning calorimeter "DSC6200" manufactured by Seiko Corp. |
| Temperature conditions | 20° C. to −30° C. (held for 30 min) at a temperature rise rate of 10° C./min; −30° C. to 50° C. at a temperature rise rate of 5° C./min |
| Sampling amount | 10 mmg |
| Cell | AL |

TABLE 7

| Proportion of KBM | TAIC (1) Melting point (° C.) | TAIC (2) Melting point (° C.) |
|---|---|---|
| 0 (blank) | 25.7 | 26.2 |
| 5 | 21.1 | 21.7 |
| 10 | 18.5 | 18.9 |
| 20 | 13.5 | 13.3 |

Note (*):
Parts by weight of KBM based on 100 parts by weight of TAIC

What is claimed is:

1. A method of storing triallyl isocyanurate, comprising the steps of mixing the triallyl isocyanurate with a silane coupling agent to prepare a composition consisting essentially of both thereof, and storing the resulting composition.

2. A method of storing triallyl isocyanurate according to claim 1, wherein the silane coupling agent is used in an amount of 5 to 30% by weight based on the weight of the triallyl isocyanurate.

3. A method of storing triallyl isocyanurate according to claim 1, wherein the silane coupling agent is γ-methacryloxypropyl trimethoxysilane.

4. A method of storing triallyl isocyanurate according to claim 1, wherein the triallyl isocyanurate comprises an organic chlorine compound represented by the following chemical formula (I) in an amount of not more than 100 ppm:

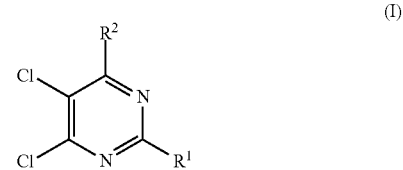

(I)

wherein $R^1$ and $R^2$ are respectively a chlorine atom or an allyoxy group with the proviso that at least one of $R^1$ and $R^2$ is a chlorine atom.

5. A method of storing triallyl isocyanurate according to claim 1, wherein the triallyl isocyanurate comprises an organic chlorine compound represented by the following chemical formula (V) in an amount of not more than 500 ppm:

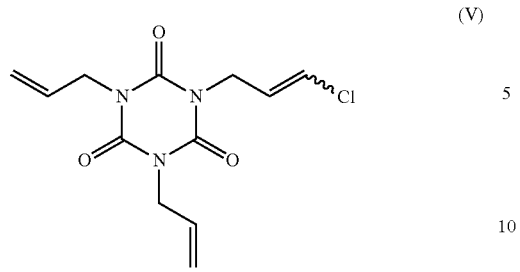
(V)
wherein a bond expressed by a wavy line indicates that the organic chlorine compound is a cis-type compound, a trans-type compound or a mixture comprising the cis-type and trans-type compounds at an optional ratio.
* * * * *